United States Patent [19]
Shibata et al.

[11] Patent Number: 4,982,415
[45] Date of Patent: Jan. 1, 1991

[54] X-RAY CT SCANNER APPARATUS

[75] Inventors: Yutaka Shibata, Tochigi; Hisanori Tohara, Ootawara, both of Japan

[73] Assignee: Kabushiki Kaisha Toshiba, Kawasaki, Japan

[21] Appl. No.: 359,892

[22] Filed: Jun. 1, 1989

[30] Foreign Application Priority Data

Jun. 3, 1988 [JP] Japan ................................. 63-135574

[51] Int. Cl.$^5$ ............................................ G01N 23/00
[52] U.S. Cl. ......................................... 378/15; 378/19
[58] Field of Search ................................... 378/4, 15, 19

[56] References Cited

U.S. PATENT DOCUMENTS

| | | | |
|---|---|---|---|
| 4,048,503 | 9/1977 | Taylor | 378/19 |
| 4,093,859 | 6/1978 | Davis et al. | 378/15 |
| 4,115,697 | 9/1978 | Honnsfield et al. | 378/15 |
| 4,259,584 | 3/1981 | Krumme | 378/15 |
| 4,298,799 | 11/1981 | Oliver | 378/4 |
| 4,323,781 | 4/1982 | Baumann et al. | 378/15 |
| 4,345,157 | 8/1982 | Klausz | 378/19 |
| 4,538,125 | 8/1985 | Beckmann et al. | 378/4 |
| 4,547,893 | 10/1985 | Gordon | 378/4 |
| 4,583,241 | 4/1986 | Walters | 378/19 |
| 4,646,333 | 2/1987 | Yoshida et al. | 378/4 |
| 4,752,691 | 6/1988 | Hawman | 378/19 |
| 4,754,468 | 6/1988 | Mori | 378/4 |
| 4,796,183 | 1/1989 | Ermert et al. | 378/4 |
| 4,845,626 | 7/1989 | Ohhashi | 378/4 |

Primary Examiner—Craig E. Church
Attorney, Agent, or Firm—Finnegan, Henderson, Farabow, Garrett, and Dunner

[57] ABSTRACT

An X-ray CT scanner apparatus comprises a rotatable support and a mounting support. The rotatable support holds an X-ray generating source and an X-ray detector in opposition to each other, and is rotated around a patient placed between the X-ray generating source and the X-ray detector. The mounting supporting supports the rotatable support in a rotatable manner. The X-ray CT scanner further comprises an X-ray data collecting unit attached to the rotatable support, a transmission member attached to both the rotatable support and mounting support, and an image-reconstructing circuit. The X-ray data collecting unit includes a data collecting circuit for collecting the X-ray projection data obtained by the X-ray detector when an X-ray CT scan is performed with respect to the patient, and also a buffer for storing the collected X-ray projection data. The transmission member transmits the X-ray projection data from the buffer to the mounting support during a rest time of the X-ray CT scan. By use of this transmitted data, the image reconstructing circuit reconstructs an image of the patient.

11 Claims, 2 Drawing Sheets

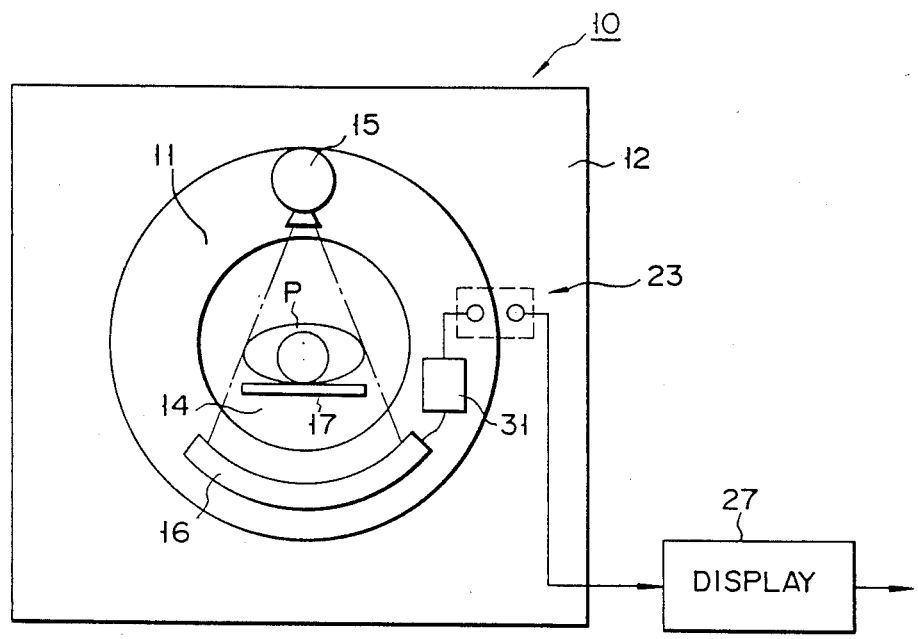
F I G. 3
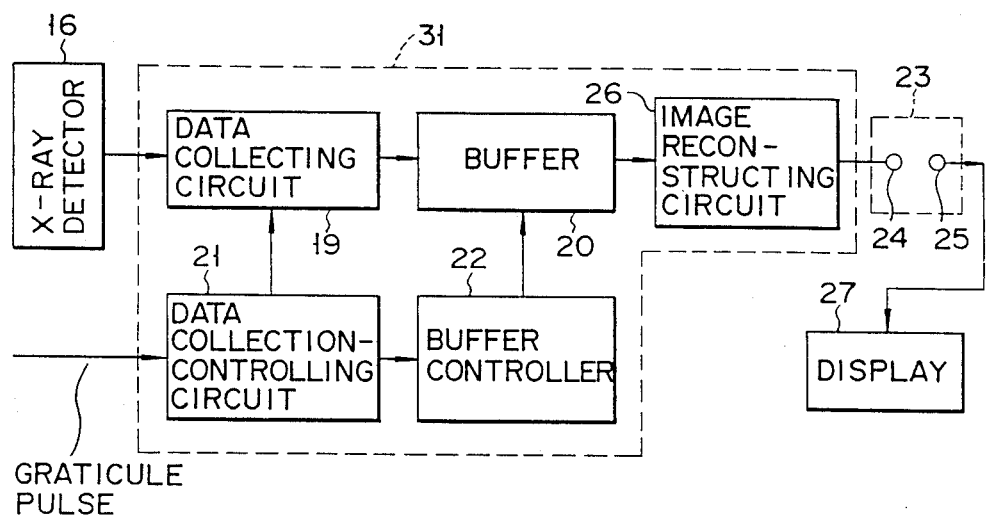
F I G. 4

X-RAY CT SCANNER APPARATUS

BACKGROUND OF THE INVENTION

1. Field of the Invention

The present invention relates to an X-ray CT scanner for collecting X-ray projection data with respect to a patient to be examined.

2. Description of the Related Art

In general, a conventional X-ray CT scanner comprises: an X-ray tube for radiating a flat, fan-shaped X-ray beam; and an X-ray detector arranged in opposition to the X-ray tube for the detection of the X-ray beam. The patient is placed between the X-ray tube and the X-ray detector, and the X-ray tube and the X-ray detector are rotated in the same direction and at the same angular velocity, with the patient as the center of rotation. During the rotation of the patient, X-ray projection data representing various-direction images of the patient is collected on the basis of the X-rays detected by the X-ray detector. After the X-ray projection data is collected in a sufficient amount, it is analyzed by a computer to calculate the X-ray absorption rate at each point of a slicing plane of the patient. In accordance with the calculated X-ray absorption rate, gradation data is provided for the collected X-ray projection data, for reconstruction of a slice image of the patient.

The CT scanner mentioned above employs either a cable or a slip ring mechanism, so as to transmit the X-ray projection data on real time from a rotatable frame portion (on which the X-ray tube and X-ray detector is supported) to a stationary frame portion. In the case where the cable is employed, a cable-handling apparatus such as that disclosed in U.S. Pat. No. 4,646,333 is required to extend or wind the cable, since the cable must be long enough not to prevent rotation of the rotatable frame portion. The use of the slip ring mechanism is disclosed in U.S. Pat. No. 4,093,859, wherein a contact brush and an annular contact are used for data transmission between the rotatable frame portion and the stationary frame portion.

As mentioned above, a conventional CT scanner apparatus employs either a cable-handling device or a slip ring mechanism. However, a CT scanner apparatus employing the cable-handling device is inevitably large as a whole since the cable-handling device occupies a wide installation space. On the other hand, the CT scanner apparatus employing a slip ring mechanism requires a high manufacturing cost since the slip ring mechanism is complex.

SUMMARY OF THE INVENTION

Accordingly, an object of the present invention is to provide a small-sized X-ray CT scanner apparatus which can be manufactured at a low cost.

To achieve this object, the present invention provides an X-ray CT scanner apparatus, comprising:

a rotatable support which holds an X-ray generation source and an X-ray detector in opposition to each other and is rotatable around a patient placed between the X-ray generation source and the X-ray detector for examination;

a mounting support or frame for supporting the rotatable support in a rotatable fashion;

a data-collecting circuit for collecting X-ray data which the X-ray detector produces when an X-ray CT scan is performed with respect to the patient during the rotation of the rotatable support;

a memory circuit for storing the data collected by the data-collecting circuit;

a data-collecting unit provided for the rotatable support;

a transmission member, provided for the rotatable support and the mounting frame, for transmitting the X-ray projection data from the memory circuit to the mounting frame during a rest time of the X-ray CT scan; and a reconstructing circuit for reconstructing an image on the basis of the transmitted X-ray projection data.

BRIEF DESCRIPTION OF THE DRAWINGS

FIG. 3 schematically illustrates the construction of an X-ray CT scanner apparatus according to another embodiment of the present invention, wherein a reconstructing circuit is provided for a rotatable support; and FIG. 4 is a block circuit diagram of the X-ray CT scanner apparatus shown in FIG. 3.

DETAILED DESCRIPTION OF THE PREFERRED EMBODIMENTS

Figure 1:
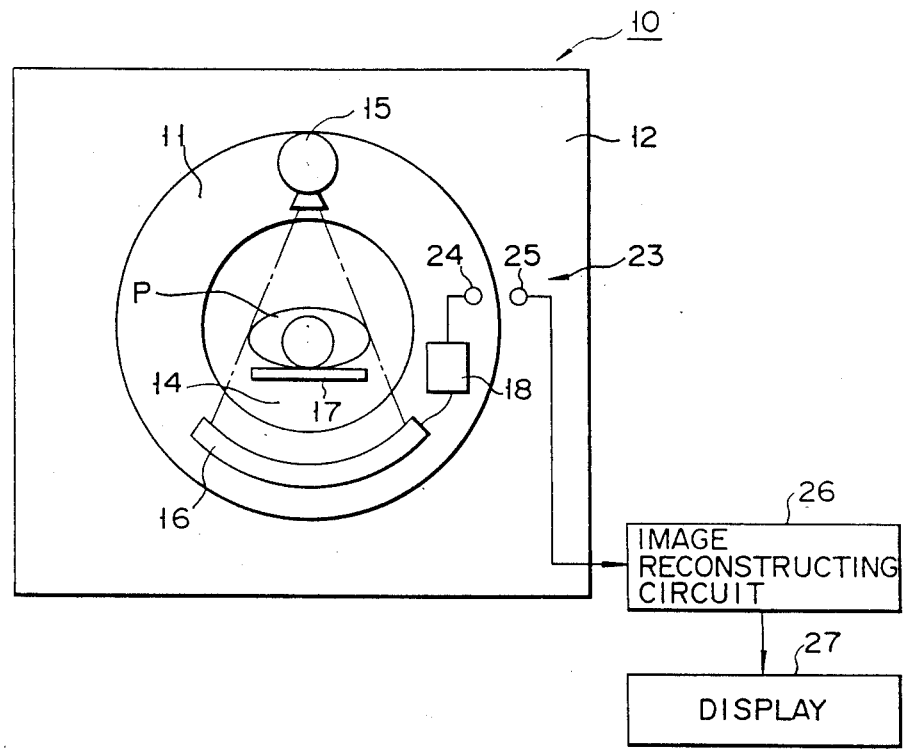
FIG. 1 schematically illustrates the construction of an X-ray CT scanner apparatus according to one embodiment of the present invention.

Referring to the X-ray CT scanner shown in FIG. 1, gantry 10 is made up of rotatable support 11, and mounting support or frame 12 which supports rotatable support 11 in a rotatable manner. Rotatable support 11 has hole (head tank) 14 in the center thereof, and X-ray tube 15 (which serves as an X-ray generation source) and X-ray detector 16 are arranged in opposition to each other, with hole 14 located therebetween. Couch 17, on which a patient to be examined is made to lie, is inserted into hole 14 for the X-ray examination of the patient, and is removed therefrom after the end of the X-ray examination. When rotatable support 11 is rotated, X-ray tube 15 and X-ray detector 16 rotates, with hole 14 as a center of rotation. At this time, X-ray tube 15 radiates X-rays toward the patient, and X-ray detector 16 detects the X-rays transmitted through the patient and outputs X-ray detection signals.

Figure 2:
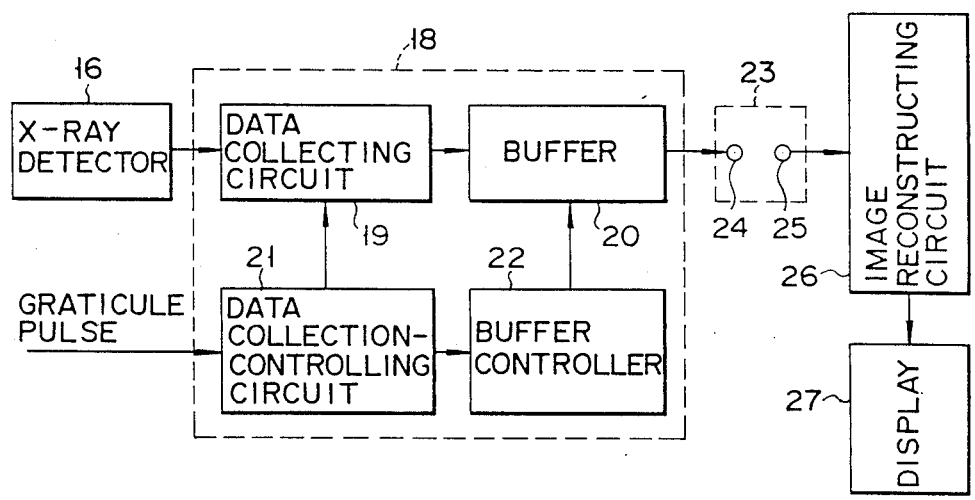
FIG. 2 is a block circuit diagram of the X-ray CT scanner apparatus shown in FIG. 1.

Rotatable support 11 is provided with data-collecting unit 18, which collects the X-ray detection signals output from X-ray detector 16. As is shown in FIG. 2, data-collecting unit 18 is made up of data-collecting circuit 19, buffer 20, data collection-controlling circuit 21, and buffer controller 22. Data-collecting circuit 19 is connected to both X-ray detector 16 and data collection-controlling circuit 21, and includes an integrator for integrating the X-ray detection signals output from X-ray detector 16, an A/D converter for converting the integrated signals into digital signals, etc. Rotatable support 11 is also provided with a pulse generator which generates graticule pulses in accordance with the rotation of support 11. In response to the graticule pulses, data collection-controlling circuit 21 controls the data collection timings of data-collecting circuit 19, such as the integration timings and the A/D conversion timings.

The output terminal of data-collecting circuit 19 is connected to buffer 20. Buffer 20 is connected to buffer controller 22 (which in turn is connected to data collection-controlling circuit 21) and is controlled thereby.

Data obtained by the X-ray CT scan of the patient is stored in buffer 20 and is read out therefrom. More specifically, in response to the graticule pulses, data collection-controlling circuit 21 supplies buffer controller 22 with a data write timing pulse. On the basis of this data write timing pulse, buffer controller 22 controls buffer 20 such that buffer 20 stores the data obtained by the X-ray CT scan. When rotatable support 11 is at rest and the X-ray CT scan is therefore stopped, the collected data is read out of buffer 20 and is supplied to data transmission unit 23.

Data transmission unit 23 is made up of signal transmitter 24 and signal receiver 25. Signal transmitter 24 is attached to rotatable support 11 It is constituted by a light-emitting element and converts the collected X-ray data read out of buffer 20 into an optical signal. Signal receiver 25 is attached to mounting frame 12. It is constituted by a photoelectric element and converts the optical signal emitted from signal transmitter 24 into an electric signal. It should be noted that the light-emitting element constituting signal transmitter 24 is rotated with the rotation of rotatable support 11. Thus, data transmission is performed only when rotatable support 11 returns to its initial position, causing the light-receiving element of signal receiver 25 to face the light-emitting element of signal transmitter 24.

The output element (i.e., signal receiver 25) of data transmission unit 23 is connected to image-reconstructing circuit 26. This circuit arranges the transmitted data into image data and displays the image data on display 27.

The operation of the above X-ray CT scanner apparatus will now be described.

Patient P to be examined is made to lie on couch 17, and is then inserted into hole 14. After determining a slice pick-up position, rotatable support 11 is rotated either clockwise or counterclockwise. Each time support 11 is rotated by a very small angle, X-ray tube 15 is driven by an X-ray tube driver circuit (not shown) to radiate an X-ray toward patient P. The X-ray transmitted through patient P is detected by X-ray detector 16. This X-ray detector generates an X-ray detection signal corresponding to the transmitted X-ray and outputs it to data-collecting circuit of unit 18. In response to the collection timing signals, i.e., 800 to 2,000 graticule pulses generated per rotation of rotatable support 11, data-collecting circuit 19 integrates the X-ray detection signal and converts it into digital data, for the collection of data. Digital data, thus collected, is supplied into buffer 20 of unit 18. This buffer stores the supplied data in response to the write timing signal supplied from buffer controller 22. In other words, buffer controller 22 controls the write timings of buffer 20 in response to the timing signals supplied from data collection-controlling circuit 21 and corresponding to the graticule pulses, so that X-ray projection data obtained with respect to the 360° directions of the patient during the X-ray CT scan (i.e., the projection data corresponding to one slice image of the patient) is stored in buffer 20.

When the X-ray projection data corresponding to one slice image has been collected in the above fashion, the rotation of rotatable support 11 is stopped, and the generation of the graticule pulses is also stopped. In this condition, couch 17 is moved lengthwise, so as to shift patient P slightly in the longitudinal axis of patient P. During the shifting of patient P, the X-ray CT scan is not performed, so that the collection of X-ray projection data is not performed. Therefore, the patient-shifting period is the rest period of the X-ray CT scan. During this period, the data stored in buffer 20 is transferred via data transmission unit 23. More specifically, when the data corresponding to one slice image of the patient has just been collected, rotatable support 11 returns to the initial position, and signal transmitter 24 faces signal receiver 25. In this condition, the data is supplied from buffer 20 to signal transmitter 24 in response to the read signal provided by buffer controller 22. Signal transmitter 24 first converts the X-ray projection data corresponding to one slice image into an optical signal, and then transmits the optical signal to signal receiver 25. Signal receiver 25 converts the optical signal into an electric signal, and transmits the electric signal to image-reconstructing circuit 26 as original X-ray projection data.

As described above, the X-ray projection data collected during the X-ray CT scan is temporarily stored in buffer 20 of data-collecting unit 18 attached to rotatable support 11, and during the rest time of the CT scan the X-ray projection data stored in buffer 20 is transmitted to image-reconstructing circuit 26 by use of the non-contact transmission between the light-emitting and light-receiving elements of data transmission unit 23.

When the rest time of the X-ray CT scan elapses after the shifting of the patient, the collection of X-ray projection data is resumed, and the X-ray projection data corresponding to the next slice image is stored in buffer 20. By repeating this procedure, the X-ray projection data corresponding to a plurality of slices of the patient is collected. The X-ray projection data, thus collected, is changed into image data by image-reconstructing circuit 26 and is displayed on display 27 as a slice image of the patient.

As may be understood from the foregoing description of the embodiment, data is collected and stored in the buffer during the X-ray CT scan, and during the rest time of the X-ray CT scan the data is collectively transferred from the rotatable frame portion of the apparatus to the stationary frame portion thereof through the non-contact transmission unit. Therefore, the CT scanner apparatus of the present invention does not have to employ such a cable or slip ring as has been required in a conventional apparatus. As a result, the gantry of the CT scanner apparatus of the invention is small, and the manufacturing cost of the CT scanner apparatus is low.

According to the second embodiment shown in FIGS. 3 and 4, data-collecting unit 31 attached to rotatable support 11 of gantry 10 includes image-reconstructing circuit 26, in addition to data-collecting circuit 19, buffer 20, data collection-controlling circuit 21 and buffer controller 22. By providing image-reconstructing circuit 26 for data-collecting unit 31, the amount of data which should be transmitted from the rotatable frame portion to the stationary frame portion can be reduced considerably.

Incidentally, the amount (M) of data to be collected by data-collecting circuit 19 is determined by the following formula:

$$M = C \times N \times B$$

where C denotes the number of channels, N denotes the number of times at which data is collected per scan, and B denotes the number of bits in the depth direction of one channel.

In general, C is 512, N is in the range of 800 to 2,0000, and B is 16. Since $M = 512 \times (800 \sim 200) \times 16$, the number of bits which should be transmitted from data-collecting circuit 26 for one slice image is considerably large. After the image reconstruction performed by image-reconstructing circuit 26, such a large amount of data is changed into data of 512×512×16 bits, which is much smaller than the amount of original data. As can be understood from this, the speed at which the data corresponding to one slice is transmitted is higher in the second embodiment than in the first embodiment.

In the second embodiment, the buffer and the buffer controller may be removed from the data-collecting unit attached to the rotatable support, with the output terminal of data-collecting circuit 19 connected directly to the image-reconstructing circuit. In this case, image data is reconstructed on the basis of the data collected by data-collecting circuit 19. Even if a cable or a slip ring is employed for the transmission of image data, the amount of data which should be transmitted is small in that case. Since, therefore, a small cable or a small slip ring suffices, the X-ray CT scanner apparatus is small as a whole and can be manufactured at a low cost.

What is claimed is:

1. An X-ray CT scanner apparatus, comprising:
    X-ray generating means for generation and radiation an X-ray toward a patient to be examined;
    X-ray detecting means for detecting the X-ray radiated from said X-ray generating means and transmitted through the patient and for producing an X-ray detection signal;
    rotatable holding means for holding said X-ray generating means and said X-ray detecting means in opposition to each other and for rotating said X-ray generating means and said X-ray detecting means with the patient as the center of rotation, to CT-scan the patient, said rotatable holding means including means for permitting the patient to be placed between said X-ray generating means and said X-ray detecting means;
    stationary holding means for holding said rotatable holding means in a rotatable manner;
    X-ray data collection means, provided for said rotatable holding means, for collecting the X-ray detection signal produced by said X-ray detecting means and producing collecting data, and having means for storing the collection data; and
    data transmission means for reading out and transmitting the collection data from said storing means of said X-ray data collection means to said stationary holding means, when CT-scan is interrupted,
    said X-ray data collecting means including means for controlling said storing means such that the collection data is stored in said storing means during a period in which the X-ray CT scan is being performed and such that the collection data is read out of said storing means and transferred to said data transmission means during a rest time of the X-ray CT scan.

2. An X-ray CT scanner apparatus according to claim 1, further comprising means for arranging the collection data transmitted by said data transmission means, so as to reconstruct an image.

3. An X-ray CT scanner apparatus according to claim 2, wherein said rotatable holding means includes means for generating graticule pulses in accordance with the rotation of said rotatable holding means, and said X-ray data collection means collects the X-ray detection signal in response to the graticule pulses.

4. An X-ray CT scanner apparatus according to claim 2, wherein said data transmission means includes optical transmission means which is made up of signal transmitter means attached to said rotatable holding means and signal receiver means attached to said stationary holding means and which performs optical transmission of the collection data produced by said X-ray data collecting means.

5. An X-ray CT scanner apparatus according to claim 4, wherein said signal transmitter means includes light-emitting element means for emitting an optical signal corresponding to the collection data, and said signal receiver means includes light-receiving element means for receiving the optical signal emitted from said light-emitting element means and converting the optical signal into an electric signal.

6. An X-ray CT scanner apparatus according to claim 1, wherein said X-ray generating means intermittently generates an X-ray in accordance with rotation of said rotatable holding means.

7. An X-ray CT scanner apparatus, comprising: pl X-ray generating means for generating and radiating an X-ray toward a patient to be examined;
    X-ray detecting means for detecting the X-ray radiated from said X-ray generating means and transmitted through the patient and for producing an X-ray detection signal; pl rotatable holding means for holding said X-ray generating means and said X-ray detecting means in opposition to each other and for rotating said X-ray generating means and said X-ray detecting means with the patient as the center of rotation, to CT-scan the patient, said rotatable holding means including means for permitting the patient to be placed between said X-ray generating means and said X-ray detecting means;
    stationary holding means for holding said rotatable holding means in a rotatable manner;
    image data output means attached to said rotatable holding means, said image data output means including means for collecting the X-ray detection signal output from said X-ray detecting means by CT-scanning the patient and transmitting the collection data, storing means for storing the collection data, and image reconstructing means for producing image data by reconstructing the collection data read out from said storing means, when the CT scan is interrupted; and
    data transmission means for transmitting the image data output from said reconstructing means of said image data output means to said stationary holding means,
    said image data output means including control means for controlling said storing means such that the collection data is stored is said storing means during a period in which the patient is CT-scanned and such that the collection data is read out of said storing means and transferred to said image reconstructing means during a rest time of the X-ray scan.

8. An X-ray CT scanner apparatus according to claim 11, wherein said rotatable holding means includes means for generating graticule pulses in accordance with the rotation of said rotatable holding means, and said X-ray data collection means collects the X-ray detection signal in response to the graticule pulses.

9. An X-ray CT scanner apparatus according to claim 7, wherein said X-ray generating means intermittently generates an X-ray in accordance with rotation of said rotatable holding means.

10. An X-ray CT scanner apparatus according to claim 11, wherein said data transmission means includes optical transmission means which is made up of signal transmitter means attached to said rotatable holding means and signal receiver means attached to said stationary holding means and which performs optical transmission of the image data produced by said image data output means.

11. An X-ray CT scanner apparatus according to claim 10, wherein said signal transmitter means includes light-emitting element means for emitting an optical signal corresponding to the collection data, and said signal receiver means includes light-receiving element means for receiving the optical signal emitted from said light-emitting element means and converting the optical signal into an electric signal.

* * * * *

UNITED STATES PATENT AND TRADEMARK OFFICE
CERTIFICATE OF CORRECTION

PATENT NO. : 4,982,415

DATED : January 1, 1991

INVENTOR(S) : Yutaka Shibata, et. al.

It is certified that error appears in the above-identified patent and that said Letters Patent is hereby corrected as shown below:

Claim 1, Column 5, line 24, "generation and radiation" should be --generating and radiating--;
Claim 1, Column 5, line 45, "collecting" should be --collection--;
Claim 3, Column 5, line 64, "2" should be --1--;
Claim 4, Column 6, line 2, "2" should be --1--;
Claim 7, Column 6, line 21, after "comprising:", "pl" should be deleted.
Claim 7, Column 6, line 27, "pl should be deleted and "rotatable" should begin a new line;
Claim 8, Column 6, line 62, "11" should be --7--;
Claim 10, Column 7, line 4, "11" should be --7--.

Signed and Sealed this

Twenty-ninth Day of December, 1992

Attest:

DOUGLAS B. COMER

Attesting Officer

Acting Commissioner of Patents and Trademarks